United States Patent
SempriMoschnig et al.

(10) Patent No.: US 7,980,758 B2
(45) Date of Patent: Jul. 19, 2011

(54) EQUIPMENT FOR NON-CONTACT TEMPERATURE MEASUREMENT OF SAMPLES OF MATERIALS ARRANGED UNDER VACUUM

(75) Inventors: Christoph SempriMoschnig, Wassenaar (NL); Marc Van Eesbeek, Oegstgest (NL); Stan Heltzel, Leiden (NL)

(73) Assignee: Organisation Intergouvernementale Dite Agence Spatiale Europeenne, Paris (FR)

( * ) Notice: Subject to any disclaimer, the term of this patent is extended or adjusted under 35 U.S.C. 154(b) by 489 days.

(21) Appl. No.: 11/922,079

(22) PCT Filed: Jun. 7, 2006

(86) PCT No.: PCT/FR2006/001305
§ 371 (c)(1),
(2), (4) Date: Mar. 21, 2008

(87) PCT Pub. No.: WO2006/131656
PCT Pub. Date: Dec. 14, 2006

(65) Prior Publication Data
US 2008/0224044 A1     Sep. 18, 2008

(30) Foreign Application Priority Data
Jun. 9, 2005  (FR) ...................... 05 51563

(51) Int. Cl.
*G01J 5/00* (2006.01)
(52) U.S. Cl. .................. 374/124; 374/121; 374/130
(58) Field of Classification Search ............. 374/121, 374/124, 130
See application file for complete search history.

(56) References Cited

U.S. PATENT DOCUMENTS

| | | | |
|---|---|---|---|
| 4,455,741 A | 6/1984 | Kolodner | |
| 5,076,707 A | 12/1991 | Neuhaus et al. | |
| 5,106,201 A | 4/1992 | Neuhaus et al. | |
| 5,219,226 A * | 6/1993 | James | 374/124 |
| 5,483,068 A * | 1/1996 | Moulton et al. | 250/340 |
| 6,098,929 A * | 8/2000 | Falbel | 244/171 |
| 2005/0006590 A1* | 1/2005 | Harrison | 250/372 |
| 2006/0071134 A1* | 4/2006 | Dent et al. | 248/274.1 |
| 2007/0076208 A1* | 4/2007 | Koo | 356/451 |
| 2007/0260422 A1* | 11/2007 | Marcus et al. | 702/172 |

FOREIGN PATENT DOCUMENTS

| | | |
|---|---|---|
| FR | 2 716 533 | 8/1995 |
| GB | 2 163 000 | 2/1986 |

* cited by examiner

*Primary Examiner* — Lisa M Caputo
*Assistant Examiner* — Mirellys Jagan
(74) *Attorney, Agent, or Firm* — Im IP Law PLLC; C. Andrew Im

(57) ABSTRACT

The invention concerns an equipment for non-contact temperature measurement (1) of samples of materials (2) arranged in a vacuum chamber (12). A UV lamp (6) illuminates the samples (2) through a window (4), so as to subject them to a predetermined thermal cycle and to perform an environmental test, in particular for materials designed for space missions. An external pyrometer measures the temperature of the samples (2) through a window (6). It is associated with a scanning module (9) including a mobile mirror, with two axes of rotation and three orthogonal axes of translation, arranged on the optical path of the infrared radiation ($R_{ir}$) so as to obtain a two-dimensional scanning of each sample (2) by means of a measuring spot focused on the surface of the samples. In a preferred embodiment, the samples are of slight thickness and locked pressed against a convex support. The whole assembly is monitored by an automatic data processing system with recorded program (10).

13 Claims, 5 Drawing Sheets

EQUIPMENT FOR NON-CONTACT TEMPERATURE MEASUREMENT OF SAMPLES OF MATERIALS ARRANGED UNDER VACUUM

RELATED APPLICATIONS

This application is a §371 from PCT/FR2006/001305 filed Jun. 7, 2006, which claims priority from FR 05 51563 filed Jun. 9, 2005, each of which is herein incorporated by reference in its entirety.

FIELD OF THE INVENTION

The invention concerns an equipment for non-contact temperature measurement of samples arranged in a vacuum chamber.

It has particular application, although non-exhaustive, for testing materials destined for space missions, and even more particularly to space missions inside the solar system or similar. The materials are then subjected to temperatures significantly higher than those recorded for earth-orbiting space missions. As non-exhaustive examples, the "BepiColombo" and "Venus Express" missions can be quoted.

To fix ideas, the following shall focus on the context of the preferred application of the invention, without restricting its scope in any way. In this context of application, it is evident that temperature is a significant factor in the degradation of materials.

BACKGROUND OF THE INVENTION

To predict the behaviour of materials used, in particular their stability over time when they are subjected to high temperatures, conventionally initial tests are conducted in laboratory conditions wherein they are subjected to a thermal cycle, according to predefined profiles of temperature variation, in a predetermined environment simulating to the best the harsh environmental conditions encountered during the aforementioned space missions: exposure to UV, VUV, EUV radiation, to X rays or even to elementary particles: electrons or protons, and to do so under high vacuum.

To achieve this objective, samples of materials are arranged generally on supports, for example on plates in a chamber having a high vacuum and are subjected to programmed heating cycles.

When tests are conducted on sample materials, the precise measurement of their temperatures, which can be taken at different points of their surface, is therefore of primordial importance.

These temperatures depend on numerous factors and parameters, such as the thermal contacts with their supports, the source of heat used, the absorption of energy particles, etc. Furthermore, the measurements can be distorted by the environment or can present different types of artifacts.

These parameters are particularly critical when tests are conducted on samples of materials of slight thickness, such as films. These tests conducted on said samples are very interesting, since they represent real standard situations: surface deposits, paint, textures, etc. The thickness of these films typically falls within the 7 to 50 µm range. In the latter case, it is evident that the quality of the thermal contact between the sample material's film and its support constitutes a major unknown factor during the test process, particularly since this thermal contact varies greatly from one sample to another.

The precision of measurements recorded also depends on the type of measurement device used and its precision.

It follows that the temperature reached by the samples of materials could, up until now, only be measured with a relative precision, incompatible with the necessities inherent in the applications concerned by the invention.

PRIOR ART OF THE INVENTION

To solve the problems concerning the measurement precision of temperatures reached by the samples of materials, it has been proposed to use thermistors of small dimension. These thermistors were put into contact with the material sample, either indirectly by means of the material sample's support, or directly using a flange, or by using an appropriate screen.

The experiment showed that these measurement methods did not produce satisfactory results.

It has also been proposed to use a camera sensitive to infrared radiation, enabling contact-free measurement through a window made of material that is transparent for these wave lengths. The window was positioned on a wall of the vacuum chamber on the test equipment. A source of ultraviolet (UV) radiation was used to irradiate and heat the samples of materials. This source was positioned outside the vacuum chamber and illuminated the samples of material through a window made of material that is transparent for UVs.

A further advantage is that this method enables the obtaining of a two-dimensional image of the material sample subjected to the test.

Nevertheless, the results obtained here were still not fully satisfactory for the following reasons:
- the surfaces of the samples of materials cannot be mapped at different thermal emissive coefficients during a simple camera scan;
- individual focussing on different samples of materials cannot be obtained; and
- a significant retroreflection of the radiation produced by the UV source and its transmission window was noted, thereby distorting the measurement.

Non-contact temperature measurement methods and devices for materials have also been proposed in prior art using pyrometers external to the test chamber. The measurement is carried out, as in the case of an infrared camera, through a window made of material that is transparent for infrared wave lengths, meaning that the optical path of the radiation can be deviated by a mirror before reaching the pyrometer.

These methods have been developed essentially to solve phenomenon of pollution produced by the materials subjected to testing during the measurement of their temperature.

Particularly, when fine layers of material are deposited in vacuum fusion, it is necessary to avoid the deposit of steam from material on the measurement window.

For example, all three patents U.S. Pat. No. 5,076,707 (Deutsche Forschungsanstalt fur Luft und Raumfahrt e.V.), U.S. Pat. No. 5,106,201 (Deutsche Forschungsanstalt fur Luft und Raumfahrt e.V.) and U.S. Pat. No. 5,209,570 (Deutsche Forschungsanstalt fur Luft und Raumfahrt e.V.), show different arrangements used to prevent or significantly reduce the contamination of the measurement window by molecules of the material arranged under vacuum.

The French patent request FR 2 716 533 (YVON and al.) shows a measurement installation that also uses a pyrometer for measuring the temperature reached by several parts of a molten glass casting, in particular before (upstream) and after (downstream) cutting with scissors. The items of cut glass, known as "gobs" or parisons, fall at high speed. It is particularly necessary to perform repetitive and sequential measurements on both parts, upstream and downstream, to compare their respective temperatures, whilst avoiding soiling the pyrometer's lens. To do so, a mobile mirror, moved by a motor, is positioned on the optical path of the infrared radiation and enables an alternative focus for downstream and upstream parts of the casting.

The devices referred to above, developed to respond to specific requirements, cannot however be transposed as they are to the invention's field of application. Particularly, they do not provide a solution for all evident requirements, in particular that of the high precision measurement of the temperature reached by a plurality of samples of different materials, particularly made up of films of very slight thickness, arranged in a vacuum chamber, nor do they enable the creation of the chart of temperatures for their surface.

To provide a solution for this specific problem, it has been tried to associate a laser emitter to the measurement pyrometer, which generates a monitoring beam, said beam enabling the alignment of the pyrometer's focus axis on the specific material sample. Nevertheless, it has been noted that this arrangement led to a procedure necessitating a high quantity of manual operations which, furthermore, are long and complex.

The methods in prior art also do not enable the elimination, or at least the very significant reduction, of the unwanted influence of the environment.

The invention aims therefore to overcome the disadvantages of devices of the prior art, and wherein some of these have been reminded and to fulfil the requirements evident in the field of thermal tests of materials destined for space missions.

SUMMARY AND OBJECTION OF THE INVENTION

The objective set by the invention is a non-contact temperature measurement equipment for a plurality of samples of materials arranged in a chamber having a high vacuum and exposed to an energy source that raises the temperature, said materials exhibiting thermo-optical properties, in particular different thermal emissivity coefficients.

To do so, according to a first feature of the invention, the temperature measurement system comprises a pyrometer associated to a two-dimensional scanning device.

In a preferred embodiment of the invention, the scanning device includes a mirror, with high reflective power for infrared wave lengths, and a component that rotates the mirror according to two orthogonal axes. The mirror is positioned on the optical path between the pyrometer and the samples, ideally such that the pyrometer's focal point be on the surface of samples. This arrangement enables a focussing on the surface of a determined material sample, on a zone of small surface. This arrangement further enables the sequential scanning, not only of a plurality of samples of materials, advantageously of materials exhibiting different emissive coefficients. It also enables the creation of a detailed chart and specifies the full surface of each of the samples of material to be tested. Lastly, it should be noted that a two-dimensional surface map of temperatures does apply for samples surface, but also apply for the surfaces of a spaceship or of various components, for example, during a thermal balance test.

In a still further preferred embodiment, the scanning device further comprises a component enabling a translation movement following the three axes of an orthonormal trihedral, one comprised in a plane that shall be referred to arbitrarily as horizontal, the other in a vertical plane, thereby increasing its degree of freedom.

In a still further preferred embodiment, when the samples of materials to be tested are made of film of slight thickness, the side of supports in contact with these samples presents a convex curve surface, such that the films can be pressed firmly against the support. It follows that a thermal contact of very high quality can be obtained. With this advantageous arrangement, the risk of samples detaching, as noted with plane supports, is thereby avoided.

There are many advantages to the measurement equipment conform with the invention including the following:
it enables non-contact measurement of samples of two-dimensional materials;
it enables the measurement of a zone of very large size inside the vacuum chamber;
it enables the raised measurement of thick samples or of a spaceship and components configured in three dimensions;
it enables measurements without handling the radiation source, for example with UV, thereby allowing measurements in a total state of balance;
it enables multiple measurements on each sample of the temperature of samples, while multiple measurements on the samples determine the uniformity of the sample's surface temperature;
it enables frequent measurements, while frequent measurements on each sample determine and ensure the stability of temperature according to time;
it enables measurements on different materials with different thermal emissivity coefficients;
it authorises the exposure of samples to a constant temperature throughout the process enabling, for example, the compensation of the radiation source's operational degradations (energy fluctuations), by means of a feedback loop acting on this source; and
due to the small dimensions authorised for the scanning device, the radiation source can be arranged very close to the samples of materials and thereby obtain an acceleration of the heating process.

The main subject of the invention is therefore an equipment for non-contact measurement of the temperature of at least one material sample arranged in a vacuum chamber, characterised in that each material sample is arranged on a support arranged on the inside of said chamber and in thermal contact with this support, in that it comprises a radiating energy source external to said chamber illuminating each sample, through a window, arranged on a wall of the said chamber, made of material that is transparent for said radiation, such that each sample is subjected to a predetermined thermal cycle, in that it comprises at least one thermo-optical temperature measurement component using an infrared radiation emitted by each sample and crossing a wall of the said chamber through a window made of material that is transparent for said radiation, in that each temperature measurement component is associated to a beam scanning module comprising a mobile mirror arranged on the optical path of said infrared radiation and two motor-powered components transmitting to said mobile mirror rotational movements following two orthogonal axes, such that said infrared radiation is deviated and a two-dimensional scanning is obtained for each sample using a measurement spot focussed on its surface.

BRIEF DESCRIPTION OF THE DRAWINGS

The invention will now be described in a more detailed manner and will refer to annexed drawings, amongst which.

DETAILED DESCRIPTION OF THE INVENTION

The following shall focus, without restricting the scope of the present invention in any way, on the context of the preferred application of the invention, unless specified to the contrary, i.e., the case of an equipment for measurement of samples of materials, arranged in a chamber having a high vacuum and subjected to environmental tests simulating a space mission during which these samples of materials will be subjected to high temperatures. More specifically, the case of samples of materials made up of films of very slight thickness, foil or similar, shall be considered.

An embodiment example of an equipment for non-contact measurement will now be described according to a preferred embodiment of the invention with reference to FIGS. 1 to 4. In these figures, the common elements have the same references and will not be described again unless necessary.

Figure 1:
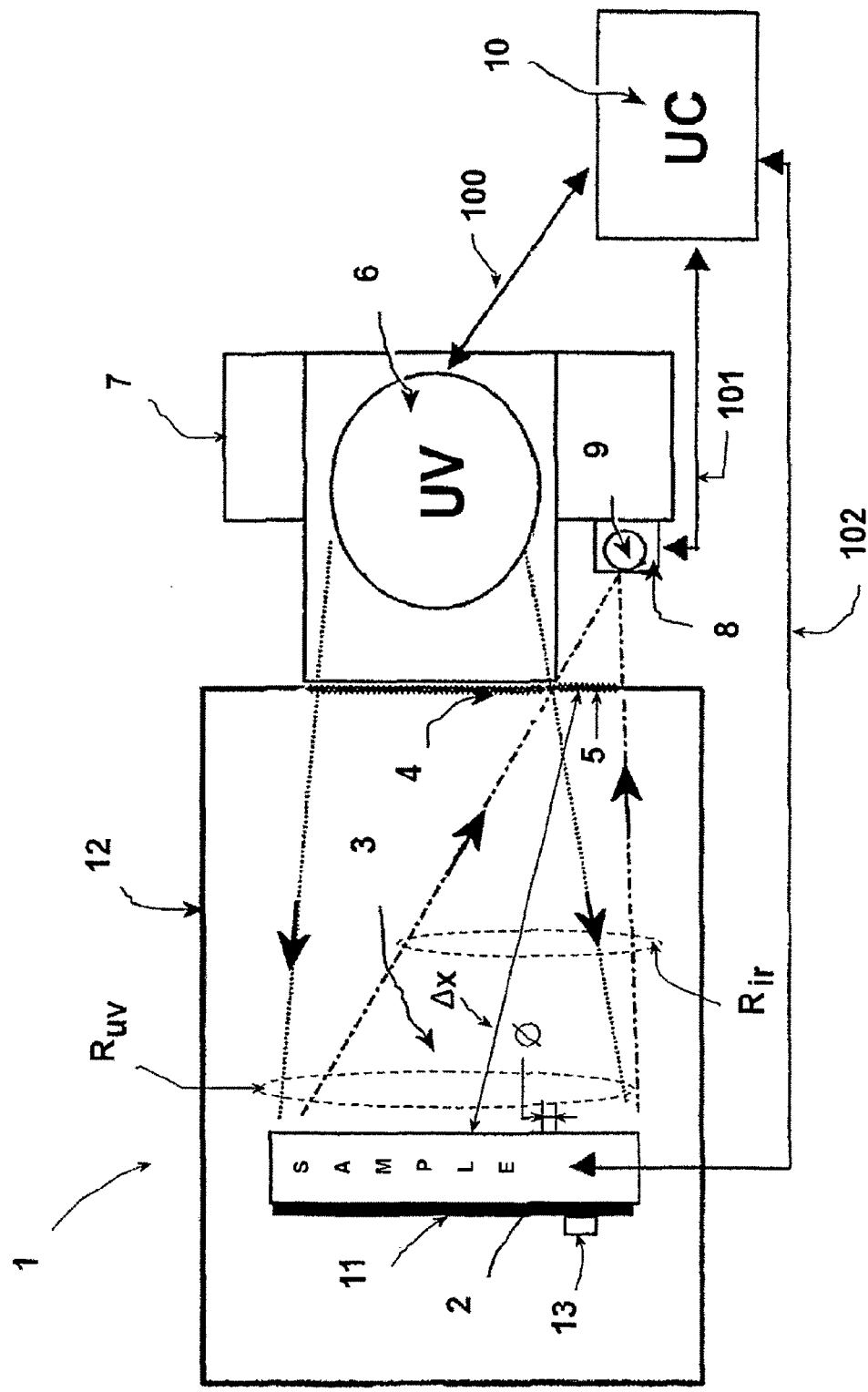
FIG. 1 illustrates schematically a configuration example of an equipment of non-contact measurement according to a preferred embodiment of the invention.

FIG. 1 illustrates schematically, as a whole, a configuration example for an equipment for non-contact measurement.

Under general reference 1, the actual measurement equipment has been represented.

The main body of the measurement equipment 1 essentially comprises a chamber 12 having a high vacuum. The components that enable the obtaining of this state are well known to skilled professionals and they will not need to be described in further detail.

Figure 2:
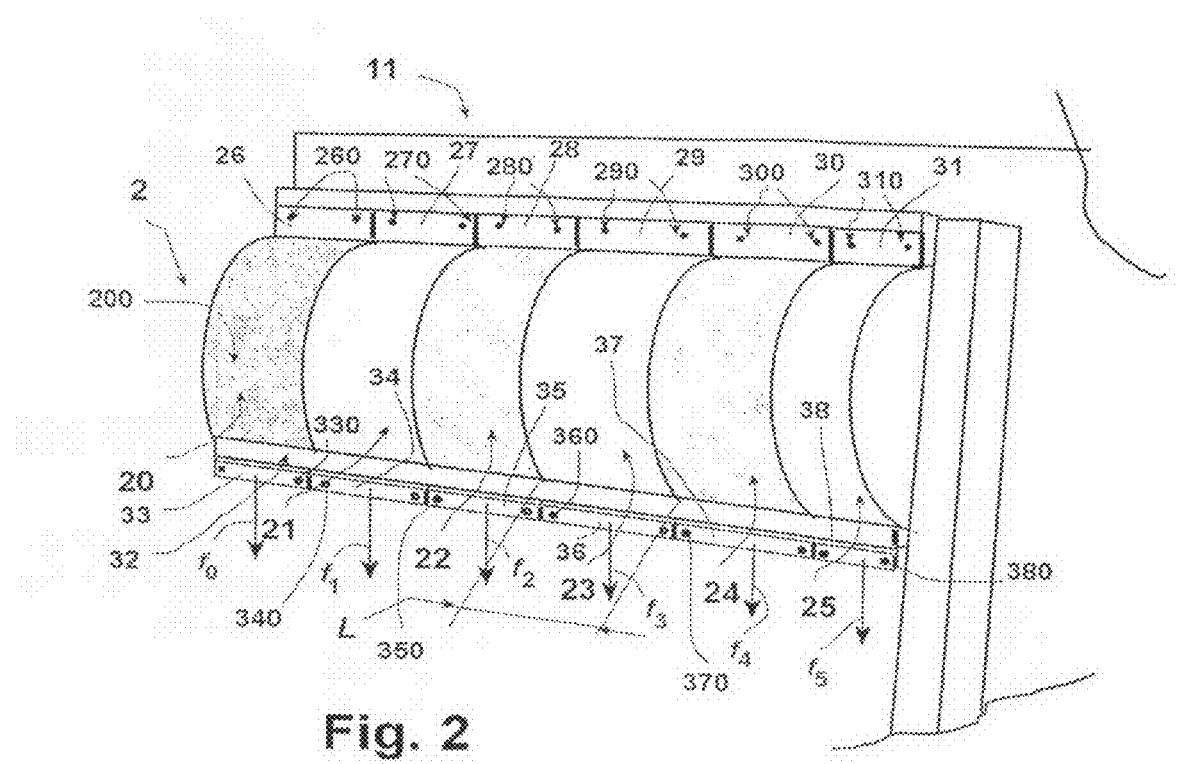
FIG. 2 illustrates schematically an embodiment example of a support component for samples of materials, integrated into the measurement equipment in FIG. 1 and more specifically destined to samples of materials in the form of films of slight thickness.

The samples of materials subjected to an environmental test, in particular to a rise in temperature, are represented in general reference 2 and are arranged on the inside of the chamber 12, on a support 11, an example of which will be detailed hereafter with reference to FIG. 2.

In the example described in FIG. 1, the source of radiation 6 is made up of a lamp emitting ultraviolet $R_{uv}$ radiation (hereafter referred to as UV to simplify the description). Nevertheless, other sources of energy can be used, it being understood that the materials, in a real space environment can be exposed, as has been specified, to different energy radiations: UV, VUV, EUV, X rays, particles, etc. The UV beam emitted by the UV lamp 6 crosses a window 4 made of material that is transparent for these wave lengths. The UV lamp 6 is positioned in an appropriate box 7.

According to a first important characteristic of the invention, the non-contact measurement instrument for the actual temperature comprises two main elements: a pyrometer 8 and a two-dimensional scanning module 9. The scanning module 9 comprises two motor-powered levels rotating a mirror 90 (see FIG. 4), coated in gold, following two orthogonal axes X and Z: rotations in the X, Y plane (arbitrarily referred to as horizontal rotation plane) and in the Y, Z plane (vertical rotation plane). The mirror 90 reflects (typically at 99%) the infrared radiation $R_{ir}$ (hereafter referred to as IR to simplify the description). The mirror 90 is positioned on the optical path between the pyrometer 8 and samples 2, ideally such that the focal point of the pyrometer 8 be on the surface of samples 2.

The $R_{ir}$ beam crosses the wall of the chamber 12 through a window 5 made of material that is transparent for the IR radiation. More generally, the window 5 is at least transparent in the field of lengths to which the detector of the pyrometer 9 is sensitive.

The IR radiation is deviated according to the tilting of the mirror around aforementioned axes X and Z. A focussing is thereby obtained on zones of small dimensions of samples of materials 2, thereby permitting unlimited scanning of the whole sector of these samples inside the chamber 12. The spatial resolution is defined by the measurement spot of the pyrometer 8 on the surface of samples of materials 2 and the angular increment of levels rotating the scanning device 9.

The area covered by the $R_{uv}$ radiation of the UV source 6 and the measurement scanning of the pyrometer 8 is referenced 3 in FIG. 1.

Another significant sub-assembly of the measurement equipment 1 consists advantageously in an automatic data processing system with software program 10 (hereafter referred to as central unit or UC to simplify the description). This CU comprises different electric and computer interfaces which monitor, in a per se known manner, the different components of the measurement equipment 1, particularly the energy delivered by the UV lamp 6 and the movements transmitted to the mirror 90 by the scanning module 9. It also receives measurement signals coming from the pyrometer and auxiliary temperature measurement components, such as one or more thermistors 13, the function of which shall be specified hereafter. The command and/or measurement signals transit via appropriate connections, under the general references 100 to 102.

Again, and per se, these arrangements are well known to skilled professionals and they will not need to be described in further detail. The CU 10 can further consist in a standard computer, only the program monitoring the components of the measurement equipment 1 needing, a priori, to be specific, but its design, equally accessible to Skilled Professionals, does not come under the context of the present invention.

The measurement spot is defined by the optical path characteristic of the pyrometer 8 and by the distance between the measured surface (surface of samples 2) and the pyrometer 8.

In an experimental embodiment, several types of pyrometer were tested. To fix ideas, the main characteristics of two of these are summarised in the TABLE I at the end of the present description. The "Type I" pyrometer is an "IN5 plus, optical 300" model and the "Type II" model is an "IPE 140, optical 3PE" model, both sold by the IMPAC Company.

The spot's diameter Ø depends on the distancing Δx of the object measured, in this case the surface of samples 2. To fix ideas, minimum and maximum lengths of the optical path inside the chamber 12 are equal, typically, to 440 and 590 millimeters respectively.

It can be noted upon examination of the TABLE I that the spot measurement dimensions depend on the pyrometer used and, where applicable, on the optical system. The choice of the pyrometer defines the lowest measurable temperature. Large samples (of several cm2) were also measured in an appropriate manner for lower sample temperatures with the "Type I" pyrometer. High-resolution scanning on small sampling sectors (several mm2) were recorded for high-temperature samples with the second pyrometer.

FIG. 2 illustrates schematically an embodiment example of support 11 according to a preferred embodiment of this support, more specifically destined for samples of materials (general reference 2) of slight thickness, films, foils or similar.

According to this embodiment, a unique support frame 2 has an external curved side 200, of convex shape. The samples of materials are made up of films of slight thickness, 20 to 25 respectively and are pressed against this convex side 200.

The equipment 2 can comprise several superimposed support frames (only the support 2 is visible in FIG. 2).

The samples, 20 to 25, are held at the upper part by narrow plates, 26 to 31, which are secured to the support 2 by pairs of screws or similar components, 260 to 310, respectively.

At the lower part, the samples, 20 to 25, are slid between the surface 200 of the support 2 and a horizontal section 32. The lower parts of these samples, 20 to 25, beneath the section 32, are wedged between pairs of narrow bars forming weights, 33 to 38, respectively, for example using pairs of screws or similar components, 330 to 380. These weights, 33 to 38, are not connected mechanically to the support 2.

This arrangement enables the films, 20 to 25, to be pressed firmly against the external side 200 of the support 2. Indeed, the weights, 33 to 38 exert forces on the films (by gravity), $f_0$ to $f_5$, dragging them downwards and obliging them to marry perfectly the convex form of the surface 200 of the support 2.

The section 32 not being connected to the samples, 20 to 25, enables free translation movement for their ends and for weights, 33 to 38. In this way, the dilatations or the constrictions (functions of different thermal coefficients) of samples, 20 to 25, due to temperature rises, are compensated. It follows that, despite correlative variations in the dimensions of samples, 20 to 25, these stay firmly held against the wall 200 of the support 2, and retain the convex shape of this support 2.

The samples can be of different materials, presenting thermo-optical properties that are also different to each other, in particular with regards the thermal emissive coefficient.

It should also be understood fully that the measurement equipment remains compatible with the temperature measurement of samples of thick materials.

As specified above, the frame 11 can comprise several supports. Advantageously, and as a non-exhaustive example, the frame 11 can comprise three supports: one upper support 2 as illustrated by FIG. 2 and two others (not shown): a lower support of the same type as the upper support (i.e., with curved surface) and an intermediary support with plane surface, more specifically destined to contain said thick samples, it being understood that for this type of sample, a good thermal contact can be obtained with greater ease due to their stronger rigidity.

Figure 3:
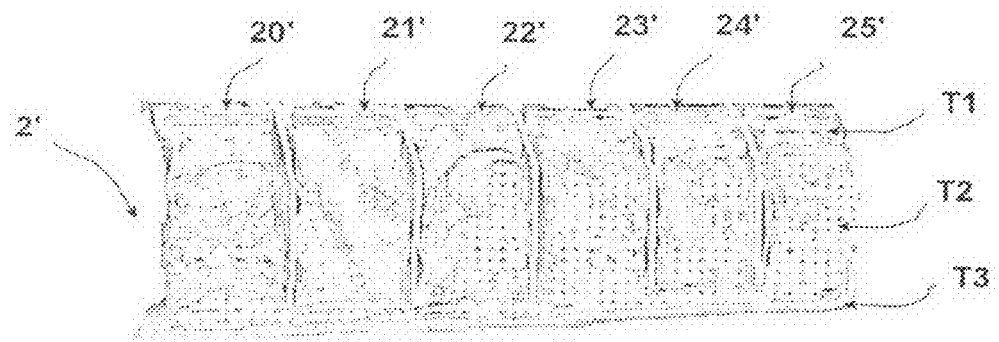
FIG. 3 illustrates very schematically a thermal chart in false colours of the surface of samples of materials positioned on the support component in FIG. 2.

An image 2' in false colours for the thermal chart of samples 20 to 25 in FIG. 2, obtained by scanning across their full surface, is illustrated very schematically by FIG. 3. The thermal images corresponding to individual samples, 20 to 25, are referenced 20' to 25', respectively. This chart generated by the CU 10 and transmitted to a peripheral device (not shown): printer or screen.

In order to better illustrate the invention, three ranges of increasing temperatures have been shown in FIG. 3, referenced $T_1$ (in the order of 200° C.) to $T_3$ (in the order of 290° C., in the example provided). Again in order to better illustrate the invention, the width of the rectangular samples, 20 to 25, is typically L=20 mm (see FIG. 2).

Two perforation holes were made (not shown) on one of the samples, of diameters 1.5 mm. The experiment shows that they can be highlighted on the thermal image 2' when this specific sample is scanned. Furthermore, the upper retaining screws, 201 to 251 (FIG. 2), have, in the example described, a width of 2 mm. The experiment shows that they are clearly discernable in image 2'. Subsequently, it can be concluded that with the specific pyrometer used for the experiment, a spatial resolution of several mm2 is possible. Nevertheless, the spatial resolution for correct temperature measurements is in reality limited to the size of the measurement spot. These, with the hypotheses used, have an approximate diameter of 4 millimeters for the aforementioned pyrometer.

Figure 4:
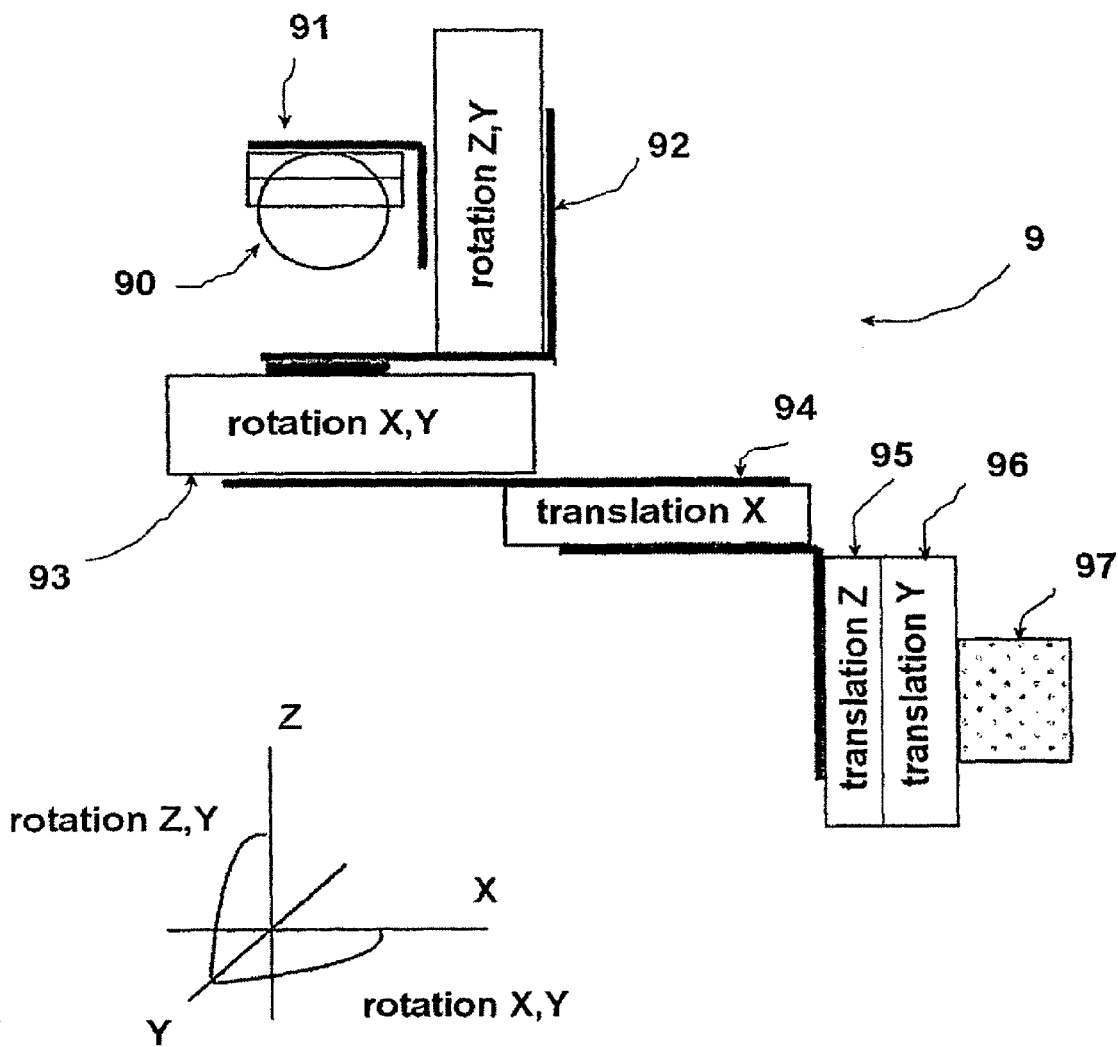
FIG. 4 illustrates schematically the configuration of a scanning device according to a preferred embodiment of the invention.

FIG. 4 illustrates in a very schematic manner the configuration of the scanning module 9, in a preferred embodiment.

The scanning module 9 comprises two rotation stages, 92 and 93, transmitting to the mirror 90 the two rotation movements previously described, around orthogonal axes X and Z (rotations in the vertical plane Z,Y and the horizontal plane X,Y). The mirror is arranged on a support 91 driven by the rotation level 92 (rotation Z, Y).

According to an advantageous characteristic of this preferred embodiment, the scanning module 9 is equipped with three additional levels, 94, 95 and 96, respectively. These three levels transmit translation movements to the mirror 90 following the respective axes, X, Y and Z, of an orthonormal trihedral XYZ. This arrangement increases the degree of freedom for the scanning module 9.

The two rotation levels, 92 and 93, are automatically commanded, by means of the central unit 10 (FIG. 1), and enable a two-dimensional scanning movement. A priori, the three translation levels, 94 to 96, are manually commanded, but there is nothing to prohibit having recourse to an automatic command.

The function of these said levels is to align the mirror 90 with reference to the pyrometer 8 and the view window 5 (FIG. 1). A priori, this concerns a unique alignment procedure which is not reiterated during the scanning movement.

The different levels are linked together mechanically by connecting plates or brackets, not expressly referenced. The different components of the module 9 are joined to a support 97, itself secured to the chamber 12 (FIG. 1).

The different rotation and translation levels, 94 to 96, can be made with standard motors, for example stepping motors (not shown). These motors are commanded, via the connection 101 (FIG. 1) by the CU 10, in open or closed loop, i.e., with feedback by comparison to instruction signals.

These different aspects are well known to Skilled Professionals and they will not need to be described in further detail.

To fix ideas, in the example described, the minimum movement increment for the two rotation levels, 92 and 93, is typically of 50 μrad (approximately 0.0030). For a maximum optical path length inside the chamber 12 of 590 mm, this angular increment corresponds to a spatial resolution of 0.03 millimeters. Still in the hypotheses used previously, if the angular increment is compared to the measurement spot of the pyrometer 8, it can be concluded that this (the spot size) constitutes the main restriction factor for the spatial resolution.

The scanning time increases quadratically with a finer resolution. Typical scanning operations were executed with an angular increment of 0.2° and took approximately 2 hours (on a sample surface of 25×20 centimeters). A scanning operation with higher resolution took two days to record with an increment of 0.05°. When the full scanning of the sampling sector is carried out, different individual sampling sectors can be chosen for complementary scanning operations. This advantageous characteristic of the invention enables the factoring in of emissivity coefficients of different samples, thereby reducing the scanning time considerably.

Another important advantage in the use of the scanning module 9 is its size. Due to the small dimensions of this scanning module 9 compared to those of pyrometers used 8, the radiation sources 6 can be positioned closer to the test installation, thereby accelerating the measurement process distinctly.

Before effective use, preliminary calibration steps need to be proceeded with on the measurement equipment 1 conform with the invention in an ambient environment. These steps will now be described with reference to the graphs in FIGS. 5 and 6.

The temperature of a specific sample, for example 20 (FIG. 2), was measured using a pyrometer 8 (FIG. 1) of aforementioned "type I". The temperature measurements were compared with those delivered by a thermistor 13 (FIG. 1) of S651PD type by the MINCO company (registered trademark). The thermistor 13 was glued to the back of the sample 20 with a fine layer of conductive adhesive of RTVS692 type marketed by the Wacker Company, as well as an aluminium strip secured to the back with an adhesive of Y966 type, marketed by the 3M Company. The sample 20 was a film of Kapton HN (registered DuPont trademark) of thickness 25 µm covered with a layer of aluminium arranged under vacuum on its rear side. The thermal emissive coefficient for this sample was 0.64. This coefficient was measured using a Gier-Dunkle (registered trademark) infrared reflectometer, model DB100, according to standard ECSS-Q70-09. This thermal emissive coefficient needs to be corrected with the infrared thermal transmission coefficient of the observation window 5 (FIG. 1), which in the example described is made of zinc selenide. This correction factor is 0.71. The corrected thermal emissive coefficient used is in this case given by the formula: 0.64×0.71=0.45. The sample 20 was fixed on a hot support plate, as in the installation described in FIG. 2. The setpoint for the hot plate was modified with 25° C. increments (FIG. 5: curve $C_1$) and the temperature measurement signals (curve $C_3$) delivered by the thermistor 13 were compared to the measurement signals (curve $C_2$) delivered by the pyrometer 8. The calibration was carried out with a continuous purge of dry nitrogen gas. The acquisition system was checked with a Fluke (registered trademark) multifunctional process calibrator, of 725 type. A measured offset of +0.3° C. was revealed, this offset being constant on the 0 to 300° C. range. The thermistor 13 was also calibrated, in a standard manner, by measuring the temperature of melting ice and boiling water. These measurements revealed no offset compared to a mercury thermometer.

Figure 5:
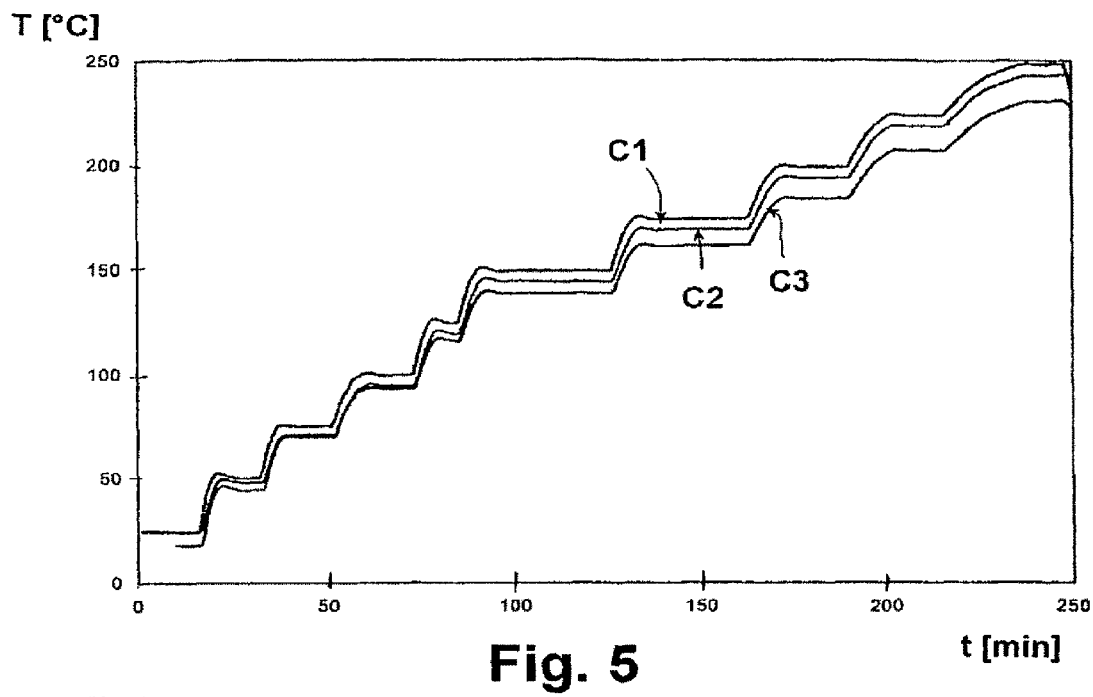
FIGS. 5 and 6 are examples of curves illustrating preliminary calibration steps for the measurement equipment to ambient pressure.

The graph in FIG. 5 then illustrates the profile of temperature variations throughout the calibration process (abscissa graduated in minutes and ordinate in ° C.). This graph shows the increase over time, in levels, of setpoints for the hot plate's temperature (curve $C_1$). As the temperature of the hot plate increases, the temperatures of the Kapton sample measured by the thermistor 13 (curve $C_3$) and the pyrometer 8 (curve $C_2$) follow this heating.

Figure 6:
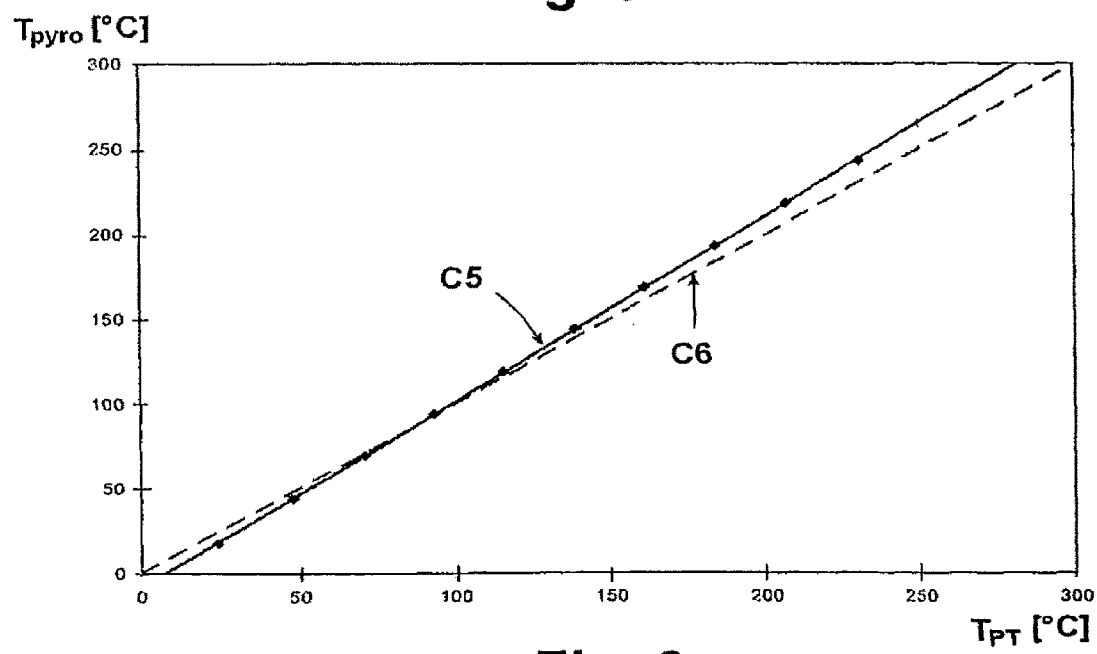

On the graph in FIG. 6, the balanced temperature of the Kapton sample measured by the pyrometer 8 (ordinate graduated in ° C.) is compared to the temperature measured by the thermistor (abscissa graduated in ° C.). The offset of 0.3° C. that was measured with the Fluke calibrator was factored into the measurements provided by the thermistor 13.

The curve $C_6$ is an ideal curve represented by the function y=x, with y and x being the ordinate and abscissa variables, respectively. The curve $C_5$ is the real curve of measurement points for the pyrometer 8, represented (in the example described) by the function y=1.1x−8.2.

Using the formula that represents the curve adjustment, the following calibration formula can be derived:

$$T_{corrected} = 0.9 * T_{pyro} + 7.5 \qquad (1)$$

$T_{corrected}$ being the corrected temperature and $T_{pyro}$ the value measured by the pyrometer 8.

Figure 7:
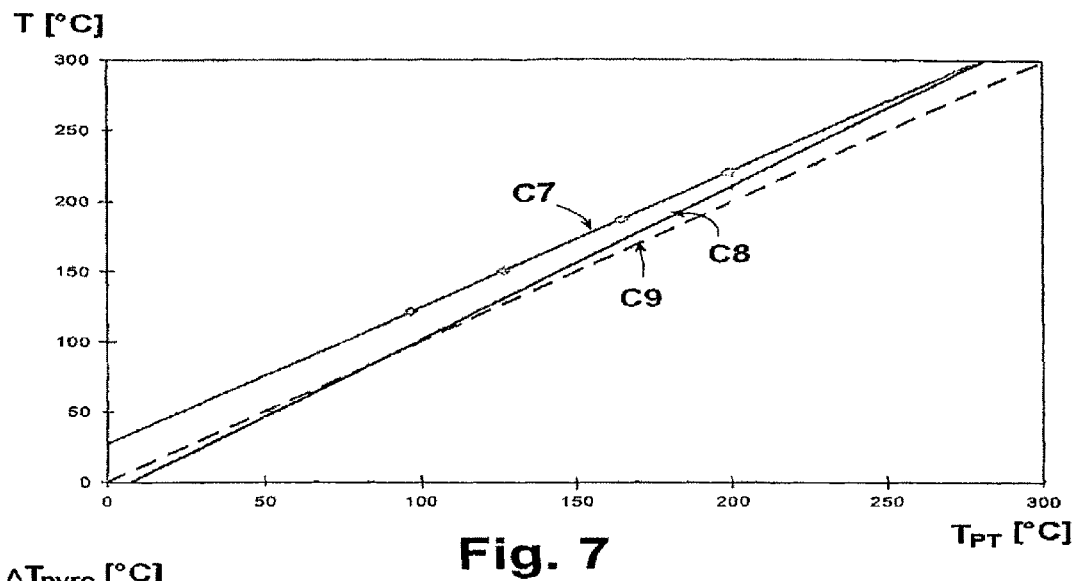
FIGS. 7 and 8 are examples of curves illustrating preliminary validation steps for measurements in test environmental conditions
Figure 8:
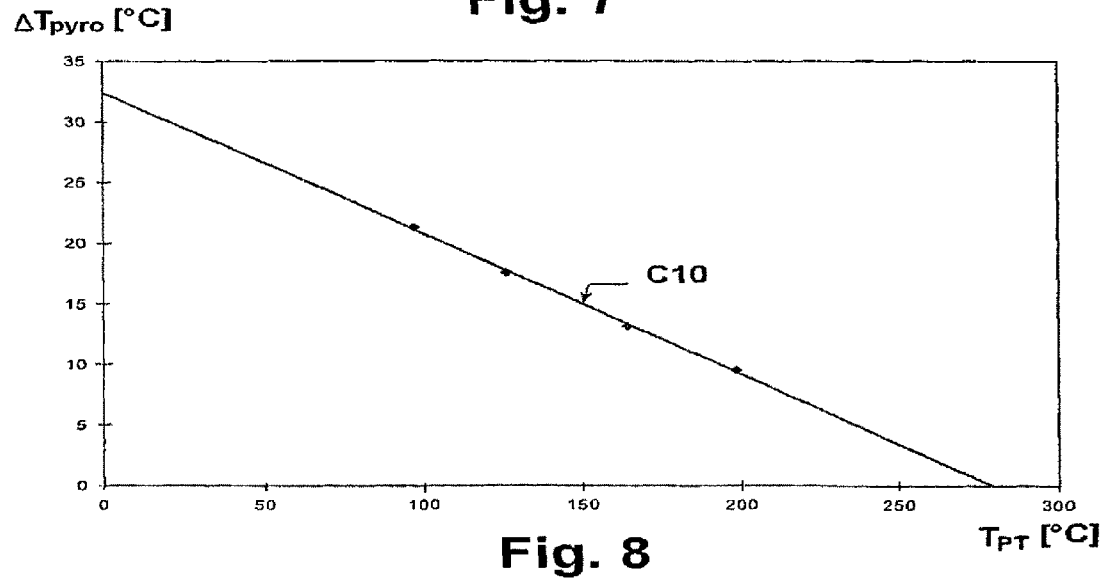

The validation of the equipment for temperature measurement conform with the invention under real test environment conditions, at least simulating to the best a space environment encountered during space missions will now be detailed, with reference to the graphs in FIGS. 7 and 8.

The graph in FIG. 7 illustrates the validation of the temperature measured in the aforementioned environmental conditions. The curve $C_7$ is the temperature curve measured by the pyrometer 8, the curve $C_8$ is the calibration curve and the curve $C_9$ is a theoretical curve representing the linear function y=x as above (with y and x ordinate and abscissa variables respectively).

The curve $C_{10}$ in the graph in FIG. 8 illustrates the difference between the temperature measured by the pyrometer 8 and the calibration data.

As specified previously, the equipment for non-contact temperature measurement 1 conform with the invention is designed to be used for environmental tests. These tests aim to study the degradation effects of electromagnetic radiation (UV, VUV, EUV, etc.) and/or particles (e, p+) on materials during space missions, at high temperature. The embodiment example described concerns more particularly tests under UV radiation, but it should be understood that the tests are not limited to only this part of space radiation. Other sources of energy can come into play.

For this purpose, samples of different materials (FIG. 2: 20 to 25) are arranged on the test equipment's support (FIG. 2: 2) and irradiated with a high-intensity UV lamp. This test is conducted in high vacuum conditions inside the chamber 12 (FIG. 1). This latter is encased in a cold mounting (not shown) which is purged with liquid nitrogen. It is expected that the thermal radiation of the surrounding components (hot) influence the measurements made by the pyrometer 8 due to the infrared reflection of the samples in the spectral range of the pyrometer. This influence is studied during preliminary validation steps as specified below.

For these measurement validation steps, the equipment for temperature measurement 1 that was used for the previous calibration steps is used, but under real environmental test conditions. These conditions comprise a high vacuum (pressure<$10^{-6}$ mbar, therefore <$10^{-6}$ hPa). The temperature of the full cold mounting is fixed at −170° C. and the high-intensity UV lamp 6 is supplied by a default voltage of 220 V. Under these conditions the evolution of the temperature of the Kapton sample on the hot support plate was measured with the thermistor 13 and with the pyrometer 8 at four different setpoints. These measurements are recorded on the graph in FIG. 7. A curve adjustment of these measurements, linear interpolated curve $C_7$, is compared to the calibration curve in the graph in FIG. 6: curve $C_5$ (curve referenced $C_8$ in FIG. 7). The temperatures measured by the pyrometer 8 should be corrected, taking into account the relation (1). The subtraction of temperatures measured by the thermistor 13 is carried out in the temperature offset as specified in graph C10 in FIG. 8. This graph shows the contribution of the environmental radiation reflected by the sample tested on the measurement of the temperature made by the pyrometer 8. It can be noted that this offset is of approximately +30° C. for an ambient sample temperature and reduces with the increase of the sample's temperature. At high sampling temperatures, a sufficient IR radiation is emitted by the sample, such that the environment's relative reflection becomes insignificant.

The curves that have just been described in detail naturally only apply to the equipment for temperature measurement described and taking into account the parameters and numerical values used as an example. Under different test conditions, it would be necessary naturally to calibrate and validate the measurements taking into account other environmental conditions, samples of materials of different thermo-optical characteristics, etc. These parameters have only been specified to better illustrate the important characteristics of the invention. More generally, the calibration curves depend on the reflection in infrared radiation IR of the tested sample, which itself depends on the material, its location on the support and the thermal conditions of the surrounding parameters. The main source of surrounding IR radiation is the heat produced by the UV lamp in the example described.

It should also be understood that the use of other types of pyrometers, of higher efficiency (such as in terms of spot size and spectral response), can enable a more precise calibration.

Lastly, an equipment fitted with two scanning pyrometers can be considered rather than an equipment fitted with only one scanning pyrometer as with the embodiment examples explicitly described, pyrometers enabling measurements under different angles. Such an equipment enables compensating infrared reflections coming from the surface to be measured.

With such arrangements, a significant improvement could be expected in terms of measurement precision.

By reading the above, it is easy to establish that the invention effectively achieves its set objectives.

There are many advantages to the equipment for non-contact measurement conform with the invention which have been summarised in the preamble of the present description. Without repeating them in full, it particularly enables two-dimensional measurements to be taken on the group of samples of the test chamber, in a repetitive manner if necessary. It enables establishing a thermal chart of the surface of these samples, with a high resolution and a high precision. This advantageous characteristic further enables the prevention of the appearance of parasite thermal radiations since the pyrometer's focussing spot, during the scanning of the surface of samples, can be of very small size.

When the samples of materials are of slight or very slight thickness (films or similar), in a preferred variation, the support of these samples is convex, which enables a thermal contact of very high quality and prevents any risks of unsticking.

It should however be understood that the invention is not restricted to the sole examples of embodiments explicitly described, notably in relation to FIGS. 1 to 8.

In particular, as specified previously, the type of radiating energy source (UV lamp in the example described) can be replaced by another type to perform tests in another part of the spectrum.

The numerical values and the examples of materials are only given to better illustrate the main characteristics of the invention and are only derived from a technological choice which is easily accessible to Skilled Professionals.

The invention is not restricted to the sole applications described explicitly, i.e., the test of materials destined for space missions. It can be used each time that temperature measurements are to be performed on samples with high precision.

TABLE I

| Pyrometer | Type I | Type II |
|---|---|---|
| Spectral bandwidth [µm] | 8 → 14 | 3 → 5 |
| Temperature range (° C.) | −32 → 900 | 50 → 1200 |
| Emissivity | 0.2 → 1 | 0.1 → 1 |
| Minimum spot diameter [mm] | Ø6 for Δx = 300 | Ø2.4 for Δx = 370 |
| Maximum spot diameter [mm] | Ø22 for Δx = 600 | Ø6.8 for Δx = 1000 |

The invention claimed is:

1. Apparatus for non-contact measurement of the temperature of a plurality material samples arranged in a vacuum chamber, wherein each material sample is arranged on a support inside of said vacuum chamber and in thermal contact with the support, comprising:
    a radiating energy source external to said chamber for illuminating said each sample with radiation, through a window on a wall of said vacuum chamber, said window being made of a material that is transparent for said radiation, such that said each sample is subjected to a predetermined thermal cycle; and
    a plurality of thermo-optical temperature measurement components for measuring temperature of said each sample using an infrared radiation emitted by said each sample and crossing the wall of said vacuum chamber through a window made of a material that is transparent for said infrared radiation; and
    wherein each thermo-optical temperature measurement component is associated with a beam scanning module comprising a mobile mirror arranged on an optical path of said infrared radiation and two motor-powered components for rotationally moving said mobile mirror along two orthogonal axes, such that said infrared radiation is deviated and a two-dimensional scanning is obtained for said each sample by measuring spot focused on surface of said each sample; and
    wherein said each sample is made of a thin film arranged on said support wherein the surface of said support in thermal contact with said each sample is convexly curved to provide a convex surface, and wherein said support comprises attachment parts in upper and lower zones of said each sample for pressing firmly against said convex surface.

2. The apparatus of claim 1, wherein said radiating energy source is a lamp emitting said radiation in the ultraviolet range.

3. The apparatus of claim 1, wherein each thermo-optical measurement component is a pyrometer.

4. The apparatus of claim 1, wherein said scanning module further comprises three motor-powered components, connected mechanically to the two motor-powered components, for translationally moving said mobile mirror along three axes of an orthonormal trihedral.

5. The apparatus of claim 1, wherein the apparatus is operable to generate a two-dimensional chart of surface temperature of three-dimensional structures.

6. The apparatus of claim 5, wherein said structure is a sample of a thick material.

7. The apparatus of claim 5, wherein said structure is a sample of material destined for space missions.

8. The apparatus of claim 1, wherein the upper attachment part comprises retaining bars and screws secured to said support; and wherein the lower attachment part comprises a horizontal section for inserting a lower end of said each sample between said horizontal section and said convex surface of said support and enabling a free translational movement of ends of said each sample; and further comprising weights, arranged under said horizontal section and secured to said each sample, for exerting forces to pull said each sample downwards by gravity and press said each sample against said convex surface, thereby compensating length variations due to dilatations or constrictions caused by temperature variations.

9. The apparatus of claim 8, wherein said each thermo-optical measurement component is a pyrometer, and further comprising:
   at least one thermistor arranged inside said vacuum chamber and in thermal contact with one of said plurality of samples or said support; and
   a calibration module for calibrating each pyrometer by comparing measurement signals received from said at least one thermistor and said each pyrometer, when each said sample is subjected to said predetermined thermal cycle.

10. The apparatus of claim 9, further comprising an automatic data processing system with software program for receiving measurement signals generated by said each pyrometer and said at least one thermistor, generating command signals, and transmitting said command signals to said scanning module and said radiating energy source.

11. The apparatus of claim 10, wherein said automatic data processing system with the software program is associated with a feedback loop for generating said command signals acting on said radiating energy source, so as to expose said each sample to a constant temperature while compensating energy fluctuations of said radiating energy source.

12. The apparatus of claim 11, wherein a plurality of samples of materials is arranged on supports inside said vacuum chamber and wherein each sample of material presents a specific thermal emissivity coefficient.

13. The apparatus of claim 12, wherein said automatic data processing system transmits command signals to said radiating energy source to subject said plurality of samples of materials to said predetermined thermal cycle, transmits command signals to said scanning module to perform a predetermined scanning of the surface of said plurality of samples of materials, and receives measurement signals from said each pyrometer to construct a two-dimensional thermal chart of the surface of said plurality of samples of materials and to convert said two-dimensional thermal chart into a thermal image in false colors for printing or display on a peripheral device of said automatic data processing system with the software program.

* * * * *